United States Patent [19]

Starr et al.

[11] Patent Number: 5,540,223
[45] Date of Patent: Jul. 30, 1996

[54] RESPIRATORY MASK FACIAL SEAL

[75] Inventors: Eric W. Starr, Pittsburgh; John R. Starr, Leechburg; Mary T. Walthour, Pitcairn, all of Pa.

[73] Assignee: Respironics, Inc., Murrysville, Pa.

[21] Appl. No.: 352,876

[22] Filed: Dec. 9, 1994

Related U.S. Application Data

[63] Continuation-in-part of Ser. No. 197,960, Feb. 17, 1994, abandoned.

[51] Int. Cl.⁶ .................................................. A62B 18/02
[52] U.S. Cl. ............................. 128/205.25; 128/206.24
[58] Field of Search ......................... 128/205.25, 206.21, 128/206.24

[56] References Cited

U.S. PATENT DOCUMENTS

| | | | |
|---|---|---|---|
| 2,011,733 | 8/1935 | Shindel | 128/206.24 |
| 2,104,016 | 1/1938 | Biggs | 128/206.24 |
| 2,317,608 | 4/1943 | Heidbrink | 128/206.24 |
| 2,323,199 | 6/1943 | Bulbulian | 128/206.24 |
| 2,433,088 | 12/1947 | Bulbulian | 128/206.24 |
| 2,465,973 | 3/1949 | Bulbulian | 128/206.24 |
| 2,706,983 | 4/1955 | Matheson et al. | 128/206.24 |
| 2,749,910 | 6/1956 | Faulconer, Jr. | 128/206.24 |
| 3,249,108 | 5/1966 | Terman | 128/206.24 |
| 4,739,755 | 4/1988 | White et al. | 128/206.24 |
| 4,907,584 | 3/1990 | McGinnis | 128/206.24 |
| 5,243,971 | 9/1993 | Sullivan et al. | 128/205.25 |

*Primary Examiner*—Aaron J. Lewis
*Attorney, Agent, or Firm*—Reed Smith Shaw & McClay

[57] ABSTRACT

A flexible, resilient respiratory mask facial seal adapted for confronting engagement with the face of a user to form an annular sealed interface encompassing a predetermined portion of the user's face. The facial seal includes a peripheral wall and an inturned flap seal. The flap seal projects radially inwardly of the peripheral wall and defines a contoured sealing surface adapted for confronting and sealing engagement with the user's face. The flap seal includes a recessed area corresponding substantially in the shape to a human nose for continuously and matingly conforming to the front and side contours of the user's nose when the facial seal is brought into confronting engagement with the user's face. The facial seal may be adapted for attachment to a respiratory mask body or may be removably placeable over the facial seal of an existing respiratory mask.

8 Claims, 3 Drawing Sheets

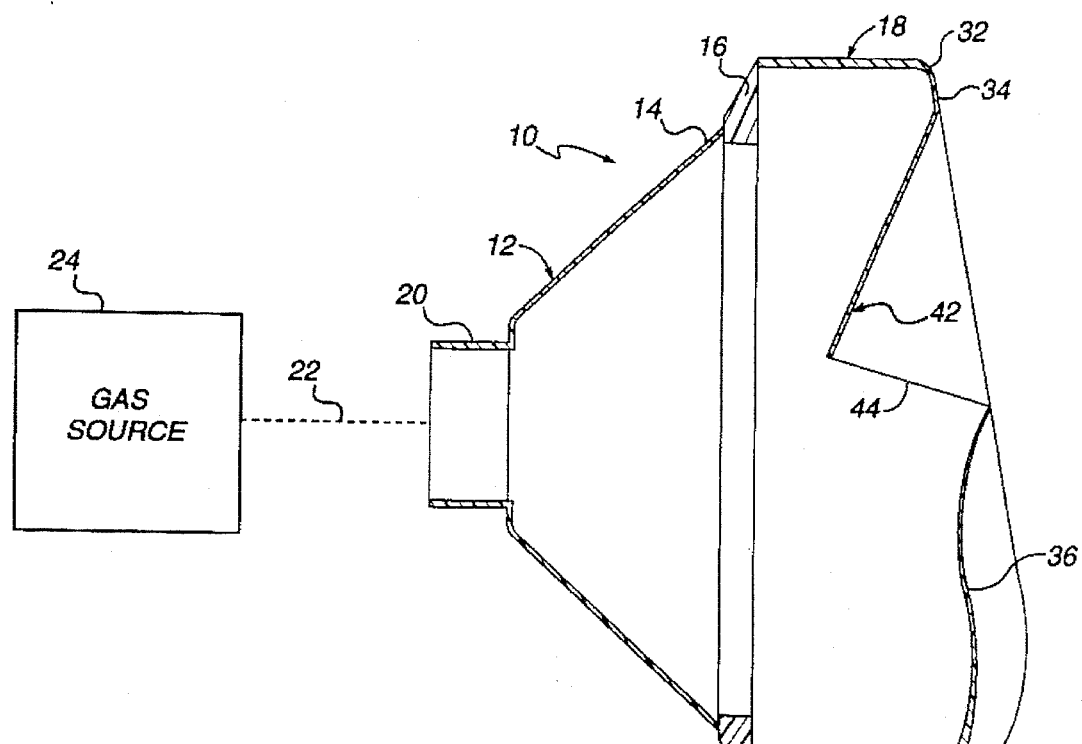
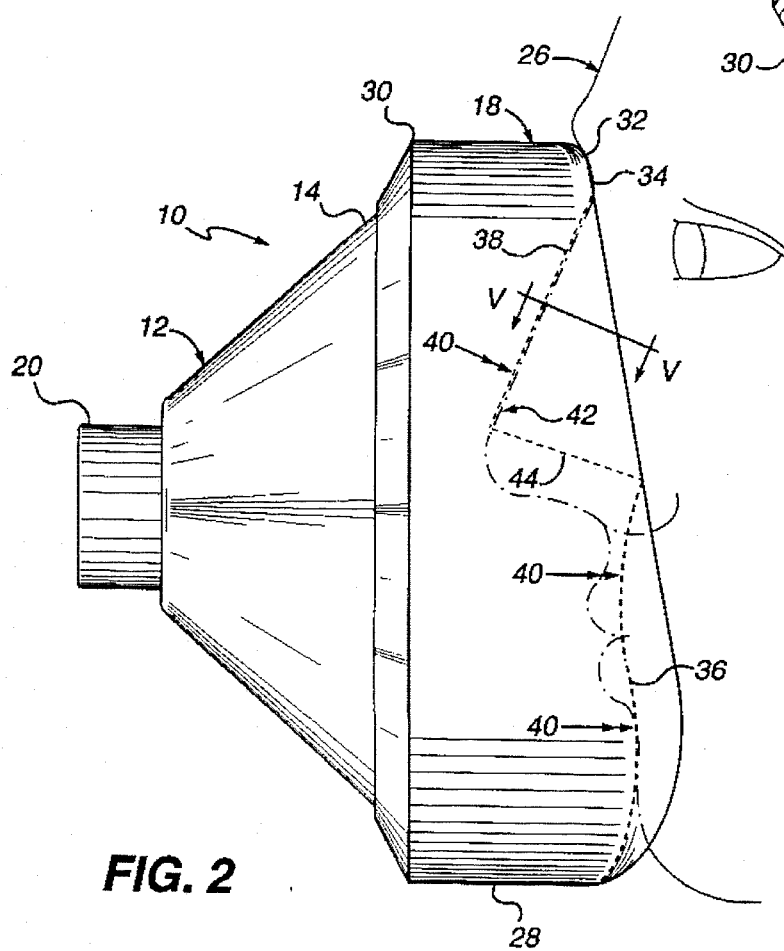

RESPIRATORY MASK FACIAL SEAL

CROSS REFERENCE TO RELATED APPLICATION

This application is a continuation-in-part of now abandoned U.S. patent application Ser. No. 08/197,960, filed Feb. 17, 1994, entitled "RESPIRATORY MASK FACIAL SEAL."

FIELD OF THE INVENTION

The present invention relates in general to respiratory masks and, more particularly, to respiratory masks having flexible seals adapted to receive portions of a user's face for preventing leakage of gas being supplied to the user.

BACKGROUND OF THE INVENTION

A variety of respiratory masks are known which have flexible seals that cover the nose and/or mouth of a human user and are designed to create a continuous seal against the user's face. Because of the sealing effect that is created, gases may be provided at positive pressure within the mask for consumption by the user. The uses for such masks range from high altitude breathing (i.e., aviation applications) to mining and fire fighting applications, to various medical diagnostic and therapeutic applications.

One requisite of such respiratory masks has been that they provide an effective seal against the user's face to prevent leakage of the gas being supplied. Commonly, in prior mask configurations, a good mask-to-face seal has been attained in many instances only with considerable discomfort for the user. This problem is most crucial in those applications, especially medical applications, which require the user to wear such a mask continuously for hours or perhaps even days. In such situations, the user will not tolerate the mask for long durations and optimum therapeutic or diagnostic objectives thus will not be achieved, or will be achieved with great difficulty and considerable user discomfort.

The prior art includes at least two types of respiratory face masks for the types of applications mentioned above. The most common type of mask incorporates a smooth sealing surface extending around the periphery of the mask and exhibiting a generally uniform (i.e, predetermined or fixed) seal surface contour which is intended to be effective to seal against the user's face when force is applied to the mask with the smooth sealing surface in confronting engagement with the user's face. The sealing surface may consist of an air or fluid filled cushion, or it may simply be a molded or formed surface of a resilient seal element made of an elastomer such as plastic or rubber. Such masks have performed well when the fit is good between the contours of the seal surface and the corresponding contours of the user's face. However, if the seal fit is not good, there will be gaps in the seal-to-face interface and excessive force will be required to compress the seal member and thereby attain a satisfactory seal in those areas where the gaps occur. Such excessive force is unacceptable as it produces high pressure points elsewhere on the face of the user where the mask seal contour is forcibly deformed against the face to conform to the user's facial contours. This will produce considerable user discomfort anywhere the applied force exceeds the local perfusion pressure, which is the pressure that is sufficient to cut off surface blood flow. Ideally, contact forces should be limited between the mask and the user's face to avoid exceeding the local perfusion pressure even at points where the mask seal must deform considerably.

The problem of seal contact force exceeding desirable limits is even more pronounced when the positive pressure of the gas being supplied is relatively high or is cyclical to high levels. Since the mask seals by virtue of confronting contact between the mask seal and the user's face, the mask must be held against the face with a force sufficient to seal against leakage of the peak pressure of the supplied gas. Thus, for conventional masks, when the supply pressure is high, headstraps or other mask restraints must be tightly fastened. This produces high localized pressure on the face, not only in the zone of the mask seal but at various locations along the extent of the retention straps as well. This too will result in severe discomfort for the user after only a brief time. Even in the absence of excessive localized pressure points, the tight mask and headstraps often may become extremely uncomfortable and user discomfort may well cause discontinued cooperation with the regimen.

Examples of respiratory masks possessing continuous cushion sealing characteristics of the type just described are provided in U.S. Pat. Nos. 2,254,854 and 2,939,458.

A second type of mask, which has been used with a measure of success, incorporates a flap seal of thin material so positioned about the periphery of the mask as to provide a self-sealing action against the face of the user when positive pressure is applied within the mask. In such a mask, the flap seal typically defines a contoured sealing surface adapted for confronting and sealing engagement with the user's face. Under the influence of a flow of pressurized gas supplied to the interior of the mask which impinges upon the surface opposite the contoured sealing surface, the sealing surface is urged into sealing contact with the user's face. With this type of sealing action, the forces which serve to hold the mask in confronting engagement on the face of the user are much lower than with the first type of mask described above. If the flap seal is capable of conforming to the contours of the user's face without forming leak paths, the mask can be used with retention straps which exert little or no net force to push the mask against the user's face. Thus, the overall sensation of constraint and confinement is dramatically reduced for the user. Such a mask, when properly adjusted, can be adapted to any positive internal mask pressure. The sealing flap will be self-sealing as long as there is no looseness in the strapping arrangement which would allow the mask to move away from the face further than the reach of the sealing flap when subjected to internal pressure.

Among the potential limitations of the second described masked type are two of note. First, the sealing flap seals by laying flat against the user's face throughout its length. This action requires a close match between the contours of the face and those of the seal. If the match is not good, the seal will be ineffective. Secondly, the normal response of one applying the mask to a user's face is to push the mask harder against the user's face if the mask does not seal. With the typical flap seal-type mask, increasing contact pressure against the user's face will not help to form an effective seal if the flap seal does not initially fit well to the facial contours. It may, however, lead to patient discomfort and other problems as described above.

Some of the principal problems one encounters when trying to apply the self-sealing flap concept to the design of the respiratory mask are related to the location of relative low points and high points in the facial contours of the user relative to the shape or contour of the flap seal surface. If the seal surface does not contact the user's face at the relative lower points, then excessive gas leakage will occur thus preventing sufficient internal gas pressure to develop to activate the sealing action of the seal flap at the low points. In the prior art, this problem has been solved for some applications by providing a variety of masks with differing seal flap shapes, sizes and contours. For example, for aircraft breathing masks, especially where expense is not a critical factor, wide variety of mask shapes and sizes may be provided to give the individual users an opportunity to find a mask offering good fit. In other breathing mask applications such as clinical use, where economic considerations may dictate a mask having the capability to accommodate a wide variety of facial sizes and contours, prior flap type seal structures have not generally been able to provide the requisite versatility.

A related problem with flap seal mask structures concerns the high points of the user's face, where the seal flap may tend to distort or collapse and fold in on itself, thus creating a channel for gas leakage, when pressure is applied in order to effect a seal at adjacent relative low points on the user's face. Even where the section thickness of the seal flap is very thin, and the material is very soft and flexible, the internal gas pressure cannot overcome some such seal flap distortion to provide the desired self-sealing.

A mask of the above-characterized flap seal type is described in U.S. Pat. No. 4,907,584, the disclosure of which is incorporated herein by reference. The mask disclosed therein includes a generally annular seal comprised of a peripheral sidewall having an inturned flexible flap seal adjacent a free end thereof, with the inturned seal being configured for confronting sealing engagement with a user's face as above described. Spaced about the peripheral seal wall are plural, upstanding, flexible ribs which serve to support the peripheral wall and an inturned portion of the seal member located generally outward of the face-engaging surface portion of the seal flap. The described seal structure is intended to permit the flap seal and peripheral sidewall to distort without experiencing any mode of seal defeating deformation such as crimping, buckling, folding or other modes of collapse. In this seal structure, the structural support ribs are located and configured in a manner to provide adequate seal flap support where seal deformation is not required (i.e., at the "low" points of the contours of the user's face) and to resiliently deform in a manner to permit easy and uniform distortion of the seal flap in those areas where distortion is necessary to accommodate "high" points on the contours of the user's face.

Other respiratory masks having flexible flap facial seats are disclosed in U.S. Pat. Nos. 4,167,185 and 4,677,977. Masks comprising both continuous cushion and flexible flap sealing features are described in U.S. Pat. Nos. 2,931,356, 3,330,273, and 4,971,051.

Despite its general efficacy in affording a desired seal against the typical user's face, the construction of the inturned flexible flap is such that the contours of certain users' faces may preclude reliable sealing by masks of this type. In this regard, the seal flap includes an opening having an enlarged lower portion to accommodate lower regions of the user's nose (and possibly the user's mouth) and an upwardly extending narrow slot portion adapted to receive the bridge of the nose. The slot bifurcates the flap into a pair of opposed flap portions adapted to lie against opposite sides of the user's nose during use. However, the front portion of the nose is left uncovered and shape of the user's nose may be such that is does not mate particularly well with the slot. For instance, the flap portions may not fully contact the sides of the user's nose or may be excessively displaced thereby which, in either case, may result in leaks in the flexible seal in the region of the nasal flap portions.

U.S. Pat. No. 4,167,185 teaches a flexible flap type mask seal which incorporates reinforcement webs or struts in the nasal flap portions of the seal to force the flap portions against the bridge of the user's nose during use. This arrangement, however, exerts localized pressure on the user's face which, in turn, results in increased user discomfort. Moreover, such a mask seal, like that proposed in U.S. Pat. No. 4,907,584, leaves the front portion of the nose fully exposed and uncovered by any sealing elements, thereby creating another potential avenue of escape for the pressurized respiratory gas.

U.S. Pat. 4,655,213 and Published PCT Application No. WO 82/03548 each describe nasal masks which substantially envelop the user's nose and provide a continuous cushion type perimetrical seal therearound. Such perimeter seals are required because the mask seal bodies are oversized to accommodate but not contact the user's nose. The seals provided by these masks are thus conceptually similar to and suffer from essentially the same drawbacks as the continuous cushion type mask seals discussed at the outset.

An advantage exists, therefore, for a respiratory mask facial seal that affords an effective yet comfortable seal for all users, notwithstanding the size and/or shape of a particular user's nose.

SUMMARY OF THE INVENTION

The present invention provides an improved flexible respiratory mask facial seal, as well as a respiratory mask incorporating such seal, which reliably and comfortably seals the facial contours, including nasal contours, of all users regardless of the configuration of a specific user's nose.

According to a presently preferred embodiment, the facial seal of the present invention comprises an annular member including a peripheral sidewall having an inturned flexible flap seal adjacent one end thereof. The inturned flexible seal includes a contoured sealing surface having formed therein a recessed area corresponding substantially in shape to that of a human nose. As is typical in flap seal-type respiratory masks, the flap seal defines a surface opposite the contoured sealing surface which is influenced by a flow of pressurized breathing gas provided from a suitable breathing gas supply to urge the contoured sealing surface into confronting and sealing engagement with the user's face. Immediately beneath the recessed area the flexible seal has an opening through which respiratory gases may pass to and from the user's nasal or oral and nasal passages during use. So constructed, the facial seal is uniquely adapted for virtually ideal confronting and sealing contact with the user's face when brought into contact therewith. The recessed area may be formed to accommodate the dimensions, e.g., length, width, prominence, convexity and bridge slope of any human nose. In all instances, however, it is preferred that the width of the recess be slightly less than that of the user's nose throughout the length of the recessed area. Hence, upon placement over the user's face, the walls of the recess become spread by the user's nose whereby the recess gently yet matingly conforms itself to the configuration of the nose while maintaining a continuous seal therewith. Further, because the spreading force is substantially evenly distributed over the entire surface area of the recess, and also because the flexible flap is formed of very soft, thin and highly pliable material, the user experiences virtually no contact pressure on his nose during usage.

The peripheral seal wall may also be provided with a plurality of upstanding flexible ribs which serve to support the peripheral wall and inturned portion of the seal member. Such ribs provide general enhancement of the capacity of the flap seal and peripheral wall to distort yet resist seal defeating deformation such as crimping, buckling, folding or other modes of collapse.

With or without additional deformation support, however, the facial seal may be secured by suitable means to any appropriately sized, substantially rigid, oral/nasal or nasal respiratory mask body to produce an improved respiratory mask having excellent face sealing capabilities. Alternatively, the facial seal may be removably placeable over the facial seal of an existing respiratory mask to improve the face sealing properties of such mask.

Other details, objects and advantages of the present invention will become apparent as the following description of the presently preferred embodiments and presently preferred methods of practicing the invention proceeds.

BRIEF DESCRIPTION OF THE DRAWINGS

The invention will become more readily apparent from the following description of preferred embodiments thereof shown, by way of example only, in the accompanying drawings, wherein:

FIG. 1 is a side elevation view, in cross section, of a respiratory mask including a first preferred embodiment of a facial seal constructed in accordance with the present invention, the respiratory mask being schematically depicted in communication with a source of respiratory gas;

FIG. 2 is a side elevation view of the respiratory mask of FIG. 1 when in confronting, sealing engagement with a user's face;

DETAILED DESCRIPTION OF THE INVENTION

Figure 3:
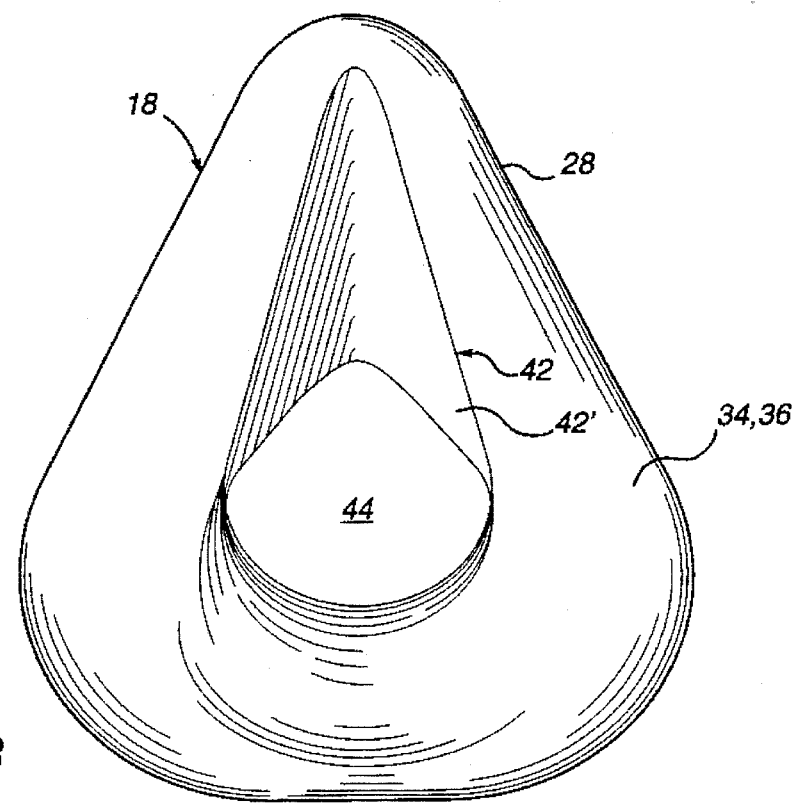
FIG. 3 is an elevation view from the exterior and looking into the interior of the respiratory mask facial seal shown in FIG. 1.

Referring initially to FIGS. 1 and 2, there is generally indicated at 10 a respiratory mask including a shell or body portion 12 having an open side 14 that defines an annular surface 16 to which is sealingly affixed a facial seal 18 constructed according to a first presently preferred embodiment of the instant invention. The mask body portion 12 is preferably, although not necessarily, a generally rigid formed structural shell, whereas facial seal 18 is a flexible, resilient unitary member which will be described in greater detail hereinafter.

Body portion 12 also defines an opening 20 or other suitable means for connecting mask 10 via conduit means (represented by dashed line 22) to a source of gas 24, e.g., a blower of other suitable means for providing a flow of pressurized breathing gas, for administration of the gas to a user 26. The mask shown is a oral/nasal or full face mask, although it is to be understood that the invention contemplates a half face mask, as will be discussed in connection with FIG. 6, which accommodates just the nasal regions of the user's face. As is conventional, although not shown, mask shell 12 also includes fastening means such as tabs, snaps, or the like to which may be connected suitable adjustable retention straps (not illustrated) for retaining the mask with respect to the user's face.

Seal 18 includes a solid, thin section, peripheral wall portion 28 having an annular base or inner end 30 configured substantially similar to the annular surface 16 of shell 12 to which it is fixedly attached. Peripheral wall portion 28 further establishes an outer end 32 generally opposite inner end 30. Adjacent the opposed or outer end 32 of peripheral wall 28 is a generally annular, inturned seal flap 34 which is integral with wall portion 28 and projects radially inwardly thereof to form a contoured sealing surface 36 (FIG. 3) adapted for confronting, sealing engagement with a user's face. The flap seal 30 also defines a surface 38 (FIG. 4) opposite the contoured sealing surface 36. When the mask 10 is internally pressurized by a flow of breathing gas from gas source 24, the pressurized gas flow (depicted by double headed arrows 40 in FIG. 2) impinges upon surface 38 to urge the contoured sealing surface 36 into confronting and sealing engagement with the user's face. As will be more fully developed later herein, the contour of sealing surface 36 closely approximates the surface contour of a user's facial structure in the area of the bridge of the nose and the user's cheek and chin structure.

For a half face mask (see the nasal mask of FIG. 6), the seal flap 34 would be contoured to accommodate, in lieu of the user's chin, the area intermediate the nose and upper lip, and the intervening areas contiguous to these. In either case, variation in user facial structure, especially in the area of the bridge of the nose, for example, makes seal flexibility necessary to accommodate the many different facial contours likely to be encountered.

Figure 4:
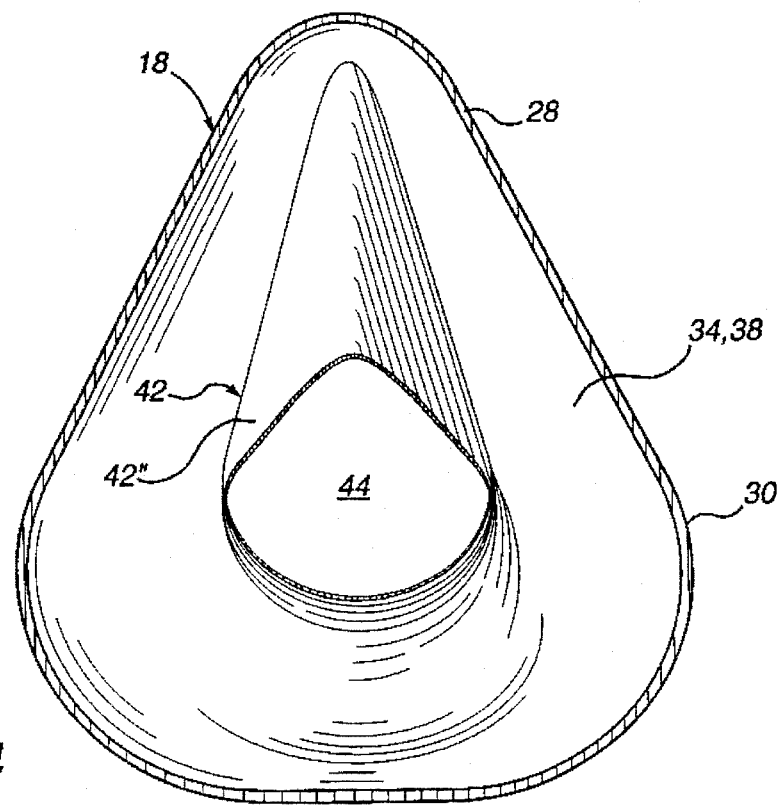
FIG. 4 is an elevation view of the interior of the respiratory mask facial seal shown in FIG. 3.

FIGS. 3 and 4 reveal in more detail the novel aspects of the respiratory mask seal 18 of the instant invention. As seen in these figures, the inturned seal flap 34 has formed therein means 42 for continuously and matingly conforming to the front and side contours of a user's nose. More specifically, means 42 comprise a recessed area integral and contiguous with the flap seal and corresponding substantially in shape to that of a human nose. Means 42 thus defines a surface 42' that is a contiguous portion of the contoured sealing surface 36. The opposite surface of means 42, identified herein by reference numeral 42" likewise defines a contiguous portion of the surface 38 against which delivered breathing gas urges the contoured sealing surface 36 into sealing contact with the user's face.

Immediately beneath the recessed area 42 the flap seal 30 defines an opening 44 through which respiratory gases may pass to and from the user's nose and mouth during use of the mask 10. Constructed as such, the facial seal 18 is uniquely adapted for virtually ideal confronting and sealing contact with user's face when brought into contact therewith.

The recessed area 42 may be formed to accommodate the dimensions including, but not limited to, length, width, prominence, convexity and bridge slope, of any human nose. In this regard, due to the flexibility and resiliency of the facial mask 18, the recessed area may be formed into a single or perhaps a few generic nasal configurations to accommodate the majority of the human population expected to use the respiratory mask 10. For less common situations, however, such as when children or adults of unusual nasal configuration require the services of respiratory mask 10, the recessed area 34 may be custom formed to accommodate these users. In any case, it is recommended that the user's nose be first accurately measured by a trained professional, e.g., a physician, nurse, respiratory therapist or other clinician, to assure that the recessed area 42 affords an effective seal yet comfortable fit with the user's face during respiratory treatment.

Figure 5:
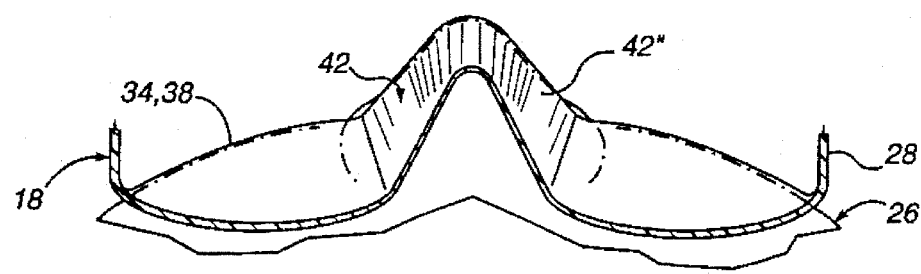
FIG. 5 is a view taken along line V—V of FIG. 2.

Further, in all instances, it is preferred that the width of the recessed area 42 be slightly less than that of the user's nose throughout the length of the recessed area. FIG. 5 illustrates that with the recessed area so configured, the walls of the recess become spread by the user's nose whereby the recessed area 34 gently yet matingly conforms itself to the shape of the nose while maintaining a continuous seal with both the front and side contours thereof. Further, because the spreading force is substantially evenly distributed over the entire surface of the recess, and also because the flexible flap 34 is formed of very soft, thin and highly pliable material, the user experiences virtually no contact pressure on his nose during usage.

Figure 6:
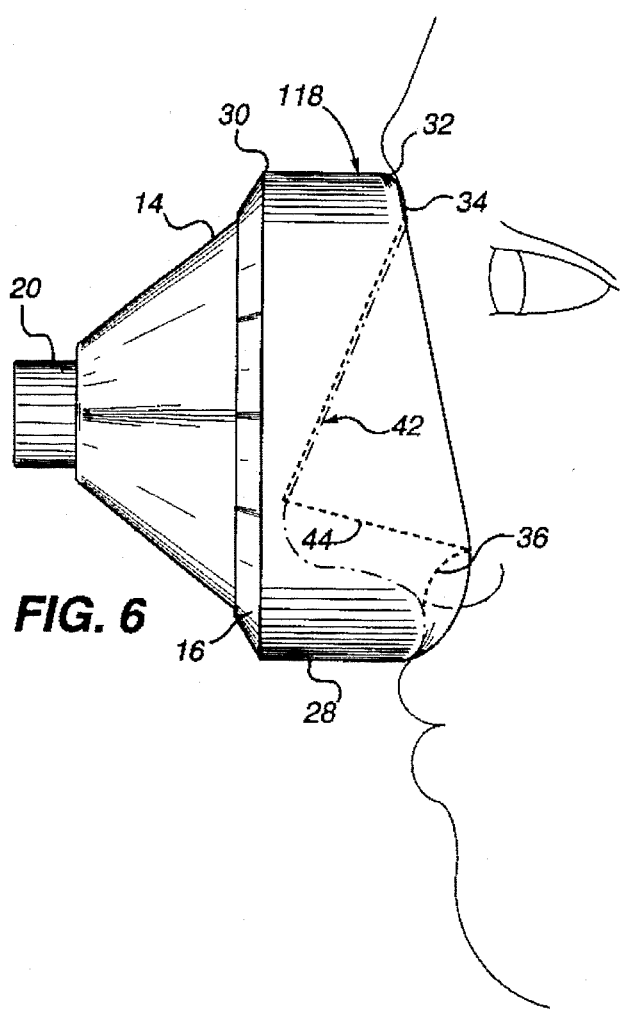
FIG. 6 is a side elevation view, similar to FIG. 2, of a respiratory mask including a second preferred embodiment of the respiratory mask facial seal when in confronting, sealing engagement with a user's face.

FIG. 6 depicts a further preferred embodiment of the facial seal of the present invention generally designated by reference numeral 118. Facial seal 118 is similar to facial seal 18 in most respects and for this reason, like references in FIG. 6 represents similar elements possessing similar functions to those described in connection with FIGS. 1 through 5. As mentioned previously, facial seal 118 is a nasal or half mask, the flap seal 34 of which establishes a seal surface 36 whose contour closely approximates the surface contour of a user's facial structure in the area of the bridge of the nose and the adjacent cheek structure. Situated opposite seal surface 36, of course, is gas flow bearing surface 38 as described above. Thus, unlike seal 18 which also accommodates the user's chin structure, seal 118 instead accommodates the area intermediate the nose and upper lip, and the interviewing areas contiguous to these. In all other respects facial seal 118 is structurally, functionally and conceptually similar to facial seal 18.

Figure 7:
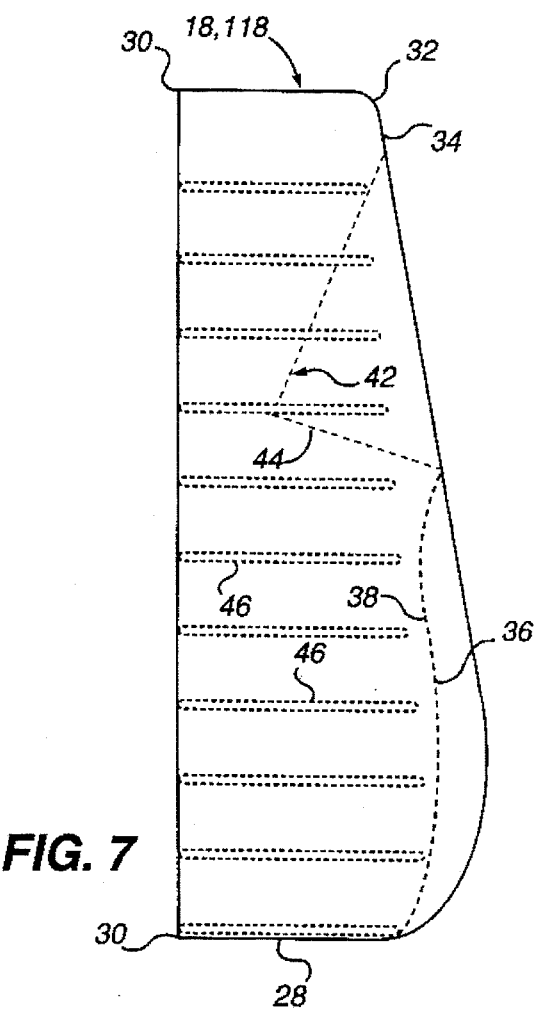
FIG. 7 is a side elevation view of a further preferred embodiment a respiratory mask facial seal according to the present invention.

FIG. 7 illustrates a further contemplated embodiment of the facial seal of the present invention which is applicable to either facial seal 18 or 118 discussed supra. As shown in FIG. 7, the peripheral seal wall portion 28 of mask 18 or 118 may also be provided with means 46 for resiliently supporting the peripheral wall portion and inturned seal flap portion 34 of the facial seal against excessive deformation. According to a presently preferred construction, means 46 comprise a plurality of upstanding flexible ribs disposed about the peripheral wall portion 28. Ribs 46 provided general enhancement of the capacity of the flap seal and peripheral wall to distort yet resist seal defeating deformation such as crimping, buckling, folding or other modes of collapse.

With or without additional deformation support, however, the facial seal 18 or 118 may be sealingly secured by suitable means to any appropriately sized oral/nasal or nasal respiratory mask body to produce an improved respiratory mask having excellent face sealing capabilities. Alternatively, facial seal 18 or 118 may be removably placeable over the facial seal of an existing respiratory mask to improve the face sealing properties of such mask.

Although the invention has been described in detail for the purpose of illustration, it is to be understood that such detail is solely for that purpose and the variations can be made therein by those skilled in the art without departing from the spirit and scope of the invention except as it may be limited by the claims.

What is claimed is:

1. A flexible, resilient respiratory mask facial seal adapted for confronting engagement with a face of a human user to form an annular sealed interface encompassing a predetermined portion of a user's face, said facial seal being adapted for operative connection to a source of breathing gas and comprising:

a peripheral wall portion having an annular inner end and an outer end opposite said inner end;

a generally annular inturned flap seal portion integral with said peripheral wall portion and located adjacent said outer end, said flap seal portion projecting radially inwardly of said peripheral wall portion and defining a contoured sealing surface adapted for confronting and sealing engagement with said predetermined portion of a user's face, said flap seal portion further defining a surface opposite said contoured sealing surface against which a flow of breathing gas delivered from a breathing gas source urges said contoured sealing surface into said confronting and sealing engagement with said predetermined portion of a user's face; and means formed in said flap seal portion for continuously and matingly conforming to the front and side contours of a nose of a user responsive to a breathing gas flow against said surface opposite said contoured sealing surface, said means for matingly conforming comprising a recessed area integral and contiguous with said flap seal portion and corresponding substantially in shape to that of a human nose.

2. The facial seal of claim 1 wherein the width of said recessed area is less than that of the nose of said user.

3. The facial seal of claim 1 further comprising means for resiliently supporting said peripheral wall portion and said flap seal portion against excessive deformation.

4. The facial seal of claim 3 wherein said means for resiliently supporting comprise a plurality of flexible ribs disposed about said peripheral wall portion.

5. A respiratory mask adapted for operative connection to a source of breathing gas and comprising:

a respiratory mask body; and a flexible, resilient respiratory mask facial seal adapted for confronting engagement with a face of a human user to form an annular sealed interface encompassing a predetermined portion of a user's face, said facial seal comprising:

a peripheral wall portion having an annular inner end sealingly attached to said respiratory mask body, and an outer end opposite said inner end;

a generally annular inturned flap seal portion integral with said peripheral wall portion and located adjacent said outer end, said flap seal portion projecting radially inwardly of said peripheral wall portion and defining a contoured sealing surface adapted for confronting and sealing engagement with said predetermined portion of a user's face, said flap seal portion further defining a surface opposite said contoured sealing surface against which a flow of breathing gas delivered from a breathing gas source urges said contoured sealing surface into said confronting and sealing engagement with said predetermined portion of a user's face; and means formed in said flap seal portion for continuously and matingly conforming to the front and side contours of a nose of a user responsive to a breathing gas flow against said surface opposite said contoured sealing surface, said means for matingly conforming comprising a recessed area integral and contiguous with said flap seal portion and corresponding substantially in shape to that of a human nose.

6. The respiratory mask of claim 5 wherein the width of said recessed area is less than that of the nose of said user.

7. The respiratory mask of claim 5 further comprising means for resiliently supporting said peripheral wall portion and said flap seal portion against excessive deformation.

8. The respiratory mask of claim 7 wherein said means for resiliently supporting comprise a plurality of flexible ribs disposed about said peripheral wall portion.

* * * * *